(12) United States Patent
Hormann (10) Patent No.: US 7,968,854 B2
(45) Date of Patent: Jun. 28, 2011

(54) DEVICE FOR STERILIZING A FLUID

(75) Inventor: Richard Hormann, Innsbruck (AT)

(73) Assignee: Wolfgang Falch, Haselgehr (AT), part interest ( * ) Notice: Subject to any disclaimer, the term of this patent is extended or adjusted under 35 U.S.C. 154(b) by 0 days.

(21) Appl. No.: 12/494,893

(22) Filed: Jun. 30, 2009

(65) Prior Publication Data

US 2009/0261264 A1   Oct. 22, 2009

(51) Int. Cl.
   *G01J 1/42* (2006.01)
(52) U.S. Cl. .................................................... 250/373
(58) Field of Classification Search ................... 250/373
   See application file for complete search history.

(56) References Cited

U.S. PATENT DOCUMENTS

| | | |
|---|---|---|
| 4,471,225 A | 9/1984 | Hillman |
| 6,264,836 B1 | 7/2001 | Lantis |
| 6,313,468 B1 | 11/2001 | Wedekamp |
| 6,669,838 B1 | 12/2003 | Baarman |
| 6,791,092 B2 | 9/2004 | Hamilton |
| 7,104,115 B2 | 9/2006 | Kahn et al. |
| 7,339,671 B2 * | 3/2008 | Peng ........................... 356/338 |
| 2001/0046461 A1 | 11/2001 | Hamilton |
| 2002/0066874 A1 | 6/2002 | Drescher |
| 2008/0156738 A1* | 7/2008 | Albrecht et al. .............. 210/748 |

FOREIGN PATENT DOCUMENTS

| | | |
|---|---|---|
| AT | 411 250 | 2/2002 |
| DE | 199 08 583 | 2/1999 |
| EP | 0 811 578 | 6/1997 |
| EP | 1 130 381 | 3/2000 |
| GB | 2 312 278 | 10/1997 |
| WO | 01/29535 | 4/2001 |
| WO | 2005/111601 | 11/2005 |

OTHER PUBLICATIONS

International Search Report issued Apr. 3, 2008 in the International (PCT) Application of which the present application is the U.S. National Stage.
Austrian Search Report issued Oct. 2, 2007 on the corresponding Austrian application.

* cited by examiner

*Primary Examiner* — David P Porta
*Assistant Examiner* — Mindy Vu
(74) *Attorney, Agent, or Firm* — Wenderoth, Lind & Ponack, L.L.P.

(57) ABSTRACT

The invention relates to a device for sterilizing a fluid and includes a container provided for receiving the fluid, at least one UV light source for the sterilization of the fluid, and at least one measuring device for determining absorption properties and/or cloudiness of the fluid. A light source is associated with the measuring device. The light from the light source to the measuring device in a first operating mode leads through the fluid at least on a partial section, and in a second operating mode on this partial section leads through a reference medium having known absorption properties and/or cloudiness.

34 Claims, 5 Drawing Sheets

DEVICE FOR STERILIZING A FLUID

BACKGROUND OF THE INVENTION

The present invention relates to a device for sterilizing a fluid, including a container provided for receiving the fluid, at least one UV light source for the sterilization of the fluid and at least one measuring device for determining absorption properties and/or cloudiness of the fluid.

It is known in the art to sterilize microbiologically contaminated media, such as for example drinking water or purified waste water, by irradiation with ultraviolet light (UV light). A device of this type has become known from AT 411 250 B in the name of the Applicant, in which a UV reference sensor and an additional UV measuring sensor are provided for measuring the light passing through a reference medium or through the fluid, respectively. The evaluation of the light signals measured by the UV measuring sensor and the UV reference sensor delivers a measuring signal which is characteristic of the intensity and if appropriate of the spectral composition of the measured UV light.

SUMMARY OF THE INVENTION

The object of the present invention is to propose an improved device of the type mentioned at the outset that is distinguished by high measuring precision and a simple construction.

According to the invention, this is achieved, in an advantageous configuration, in that a light source is associated with the measuring device. The light from the light source leads to the measuring device in a first mode of operation at least on a partial section through the fluid, and leads in a second mode of operation on this partial section through a reference medium having known absorption properties and/or cloudiness.

In this way, in the first mode of operation, the emitted light from the light source can be passed through the partial section filled with the fluid, the intensity and if appropriate the spectral distribution of the light passing therethrough being detected by the measuring device as a characteristic measured value. In the second mode of operation, on the other hand, the emitted light from the light source can be passed through the partial section filled with the reference medium—corresponding to the same partial section of the first mode of operation. A reference value which is characteristic of the light irradiated from the light source can be calculated from the value, measured in the second mode of operation, for the intensity and if appropriate for the spectral distribution.

As a result of the detection of a measured value and the determining of a reference value, as well as checking the operativeness of the light source, a statement can be made concerning the light absorption properties of the fluid to be sterilized and thus concerning the fluid itself. This draws on the fact that a large number of organic substances absorb ultraviolet light. This provides the particular advantage that the light beam for the detection of the measured value emits from the same area of the light source than the light beam of the light source when determining the reference value. This compensates for all the changes which influence the measured variables of the components, lying in the beam path, outside the measuring interval (time lag between determining the measured value and determining the reference value). In particular, spatial and temporal inhomogeneity of the radiation given off by the light source is compensated for.

According to a preferred exemplary embodiment of the invention, precisely one measuring device can be arranged for the first and second mode of operation. As a result of the detection of the measured value of the light passing through the fluid and the detection of the light passing through the reference medium, one and the same measuring device allows in a precise manner, when determining the reference value, a direct comparison of the measured value and reference value and thus an evaluation of the fluid to be sterilized. In addition, the same ambient conditions (for example identical locations for detection of the light beam emitting from the light source and the same ambient temperatures) prevail during detection of the measured value and the reference value in order to prevent falsification of the test result—in particular as a result of the temperature dependency of the sensors. A separate measuring device for detecting the measured value and for detecting the reference value is in this case not strictly necessary, allowing the device to be produced at lower cost.

Advantageously, provision is made for the reference medium to be a fluid which is different from the fluid to be sterilized and has known absorption properties and/or known cloudiness. In this connection, it may be expedient if the reference medium is air. When selecting the reference medium, care is generally taken to ensure that the reference medium has constant transmission properties for the UV light irradiated by the UV light source. In selected variant embodiments, provision may also be made for the reference medium to have defined filter properties with respect to the UV light irradiated by the UV light source. This can, for example, be used to configure defined light wave length ranges so as to be more effectively evaluable.

The light source of the measuring device is expediently a UV light source. An advantageous configuration of the invention is obtained in that the light source of the measuring device is the UV light source used for the sterilization of the fluid.

It can be provided that the measuring device comprises a measuring chamber for receiving the fluid and/or the reference medium. In this case, it is beneficial if the measuring chamber for receiving the fluid to be sterilized is the same measuring chamber as that for receiving the reference medium. A further development of the invention is obtained in that the measuring chamber is arranged at least in certain regions, preferably entirely, spatially outside the container provided for the sterilization of the fluid. Thus, the measuring chamber and/or the measuring device is arranged per se outside the chamber system provided for the treatment of the fluid, thus allowing temperature-induced fluctuations to be substantially prevented. According to a further exemplary embodiment, provision may be made for the measuring device to be coolable by a cooling device, at least in certain regions.

An advantageous variant of the invention is obtained in that a light source is associated with the measuring device, the light from the light source leading to the measuring device at least on a first partial section through the fluid and leading on this or a separate partial section through a reference medium having known absorption properties and/or cloudiness. The light from the light source can be irradiated for the first and second partial section from the same region of the light source.

A further expedient variant of the invention is obtained in that a device for generating at least two regions having different pressure ratios is arranged in the chamber system, preferably a restrictor. Fluid from the region of the higher pressure ratio of the fluid can be supplied to the measuring device and can subsequently be supplied to the region of the lower pressure ratio of the fluid.

Finally, a further variant of the invention is characterized in that at least one partial section, which is movable relative to the UV light source, is provided in the chamber system. In a first operating position of the partial section, the light from the UV light source can be supplied to the measuring device over the partial section filled with the fluid to be sterilized. In a second operating position of the partial section, the light from the UV light source can be supplied to the measuring device over the partial section filled with a reference medium.

BRIEF DESCRIPTION OF THE DRAWINGS

Further details and advantages of the present invention will be explained in more detail with the aid of the subsequent description of the figures, in which.

DETAILED DESCRIPTION OF THE INVENTION

Figure 1:
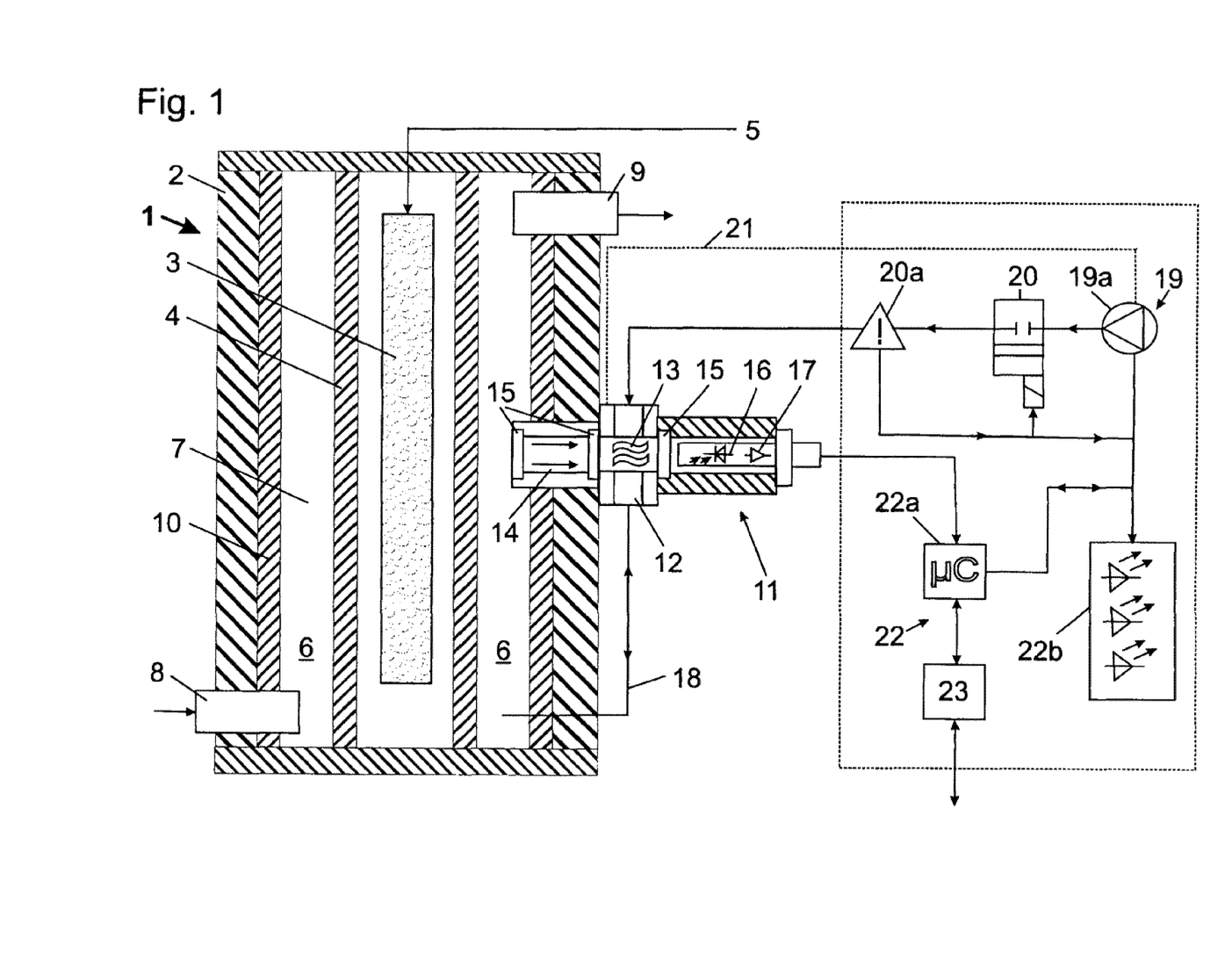
FIG. 1 shows an embodiment of a device according to the invention for sterilizing a fluid.

FIG. 1 is a schematic vertical section through an exemplary embodiment of a device 1 according to the invention. A tubular, elongated UV light source 3, which is surrounded by a transparent cylindrical quartz glass vessel 4, is arranged in a cylindrical container 2, for example a PVC tube. Reference numeral 5 denotes generally the electrical terminal and also the control devices of the UV light source 3. The UV light source 3 mounted in the quartz glass vessel 4 is surrounded by a chamber system 6 through which the fluid 7 to be sterilized flows. The container 2 has an inlet 8 into the chamber system 6 for the fluid 7 to be sterilized and also an outlet 9 for the substantially sterilized fluid 7. The fluid 7 to be treated is therefore sterilized, as it travels between the inlet 8 and inlet 9, by the UV light from the UV light source 3. In addition, in order to lengthen the duration of the action of the UV light, and thus the sterilization of the fluid 7 to be treated, provision may also be made for the fluid 7 to be treated to be guided in counterflow twice or a plurality of times past the UV light source 3. In principle, this increases the irradiation time and thus improves the sterilization attained overall.

A measuring device 11 comprises a measuring chamber 12 with a partial section 13 which is arranged therein. The partial section 13 is fillable in a first mode of operation with a sample of the fluid 7 to be sterilized and in a second mode of operation with a reference medium—for example air. The measuring chamber 12 having the partial section 13 is arranged completely outside the container 2 provided for the sterilization of the fluid 7. A light channel 14, having measuring windows 15 made of transparent quartz or sapphire glass, penetrates the high-grade steel tube 10 along with the container 2, so that light from the UV light source 3 can be supplied to the measuring chamber 12 or the partial section 13, respectively. The light emitted by the rod-shaped UV light source 3 therefore passes into the partial section 13 through the light channel 14 and subsequently strikes a measuring sensor 16 comprising, by way of example, at least one photodiode. Furthermore, the measuring device 11 has a signal amplifying device 17 for boosting the measuring signals.

In a first mode of operation according to the present invention, the measuring device 11 can be used to detect the intensity and if appropriate the spectral distribution of the light from the UV light source 3, the light passing through the fluid 7 to be sterilized, as a characteristic measured value. For this purpose, the device 1 has a sample taking device for removing fluid 7—preferably fluid samples—from the container 2, which sample taking device can be used to remove the fluid 7 from the container 2 and supply it to the measuring chamber 12 or the partial section 13 via a line 18. The sample taking device comprises for this purpose a conveyor device 19 with a pump 19a for generating a reduced or excess pressure of a control medium for the transportation of the fluid 7 in the line 18. Depending on the switching position of the valves 20, the pump 19a generates a reduced pressure with which the fluid 7 is drawn out of the container 2 or else a pressure with which, after the measuring has been carried out, the fluid 7 is pressed out of the measuring chamber 12 and preferably transported back into the container 2. Reference numeral 20a denotes generally a safety device (for example a pressure switch, a float or the like).

In the first mode of operation, a reduced pressure generated by the pump 19a now draws a fluid sample out of the container 2 into the measuring chamber 12. A fluid detector device 21 detects the level of the fluid 7 in the measuring chamber 12, the pump 19a being switched off if the level of the fluid in the measuring chamber 12 is reached or exceeded, so that the fluid 7 does not overflow in the measuring chamber 12. The fluid detector device 21 can comprise for example at least two electrodes which are arranged in the measuring chamber 12 and trigger, on contact with the fluid, a switching signal for switching off the conveyor device 19. The fluid 7, which is now located in the measuring chamber 12 or in the partial section 13, is now exposed to the UV radiation which is given off by the UV light source 3 and enters through the measuring windows 15. In this case, the intensity of the UV radiation, which has passed through the fluid 7 and strikes the measuring sensor 16, depends on organic substances/particles present in the fluid 7. The measuring sensor 16 converts the impinging radiation energy into electrical current which is intensified by the signal amplifying device 17 and forwarded as a voltage signal to an evaluation device 22 (for example an analog/digital converter of a microcontroller 22a), where it is stored as a measured value.

After the measurement of the UV radiation passing through the fluid 7 in the measuring chamber 12, the fluid 7 is pressed back out of the measuring chamber 12 and preferably into the chamber system 6 of the container 2 by a pressure generated by the pump 19a and released by the valve 20. The radiation given off by the UV light source 3 enters the measuring chamber 12, which is now filled with air, or the partial section 13, which is filled with air, through the measuring windows 15. Once it has passed through the partial section 13, which is filled with air, the light from the UV light source 3 strikes the photodiode of the measuring sensor 16. The photodiode converts the impinging radiation energy into electrical current which is intensified by the signal amplifying device 17 and forwarded as a voltage signal to the A/D converter of the microcontroller 22a, where it is stored as a reference value.

In a subsequent step, the microcontroller 22a calculates the spectral extinction coefficient (SEC) from the stored measured value and reference value and from the measuring path (distance between the measuring windows 15 in the measuring chamber 12). The evaluation device 22 comprises a display device 22b which has a plurality of light emitting diodes and serves to display the measured measuring signals, in particular the SEC value. In addition, the data can be provided to an external data processing system (for example a personal computer) via an interface 23.

An advantageous configuration of the invention allows a reference value, which is characteristic of the light irradiated by the light source 3, to be calculated from the value measured in the second mode of operation. The reference value provides unambiguous information concerning the light irradiated by the UV light source 3. It is possible to determine the lamp power and the ageing of the UV light source 3 based on a comparison of the reference value with the radiation power measured at the start of operation and given off by the UV light source 3.

The spectral absorption coefficient (SAC), which is a measure of the dissolved organic substances contained in the fluid 7, can be detected as a measurable variable. As a result of the dissolved organic substances which are present in the fluid 7 and generally have an absorption maximum at 260 nm, the UV radiation is attenuated as it passes through the fluid 7. The SEC value measured by the measuring device 11 contains the SAC.

As the UV radiation is attenuated also as a result of scattering of the particles present in the fluid 7, the SEC value measured by the measuring device 11 (UV probe) is also a measure of the cloudiness of the fluid 7. The SEC value is therefore a measure of both the dissolved organic substances contained in the fluid 7 (SAC) and of the cloudiness of the fluid 7. Based on the SEC, it is not possible to decide whether the fluid 7 is organic-laden or cloudy.

Figure 2:
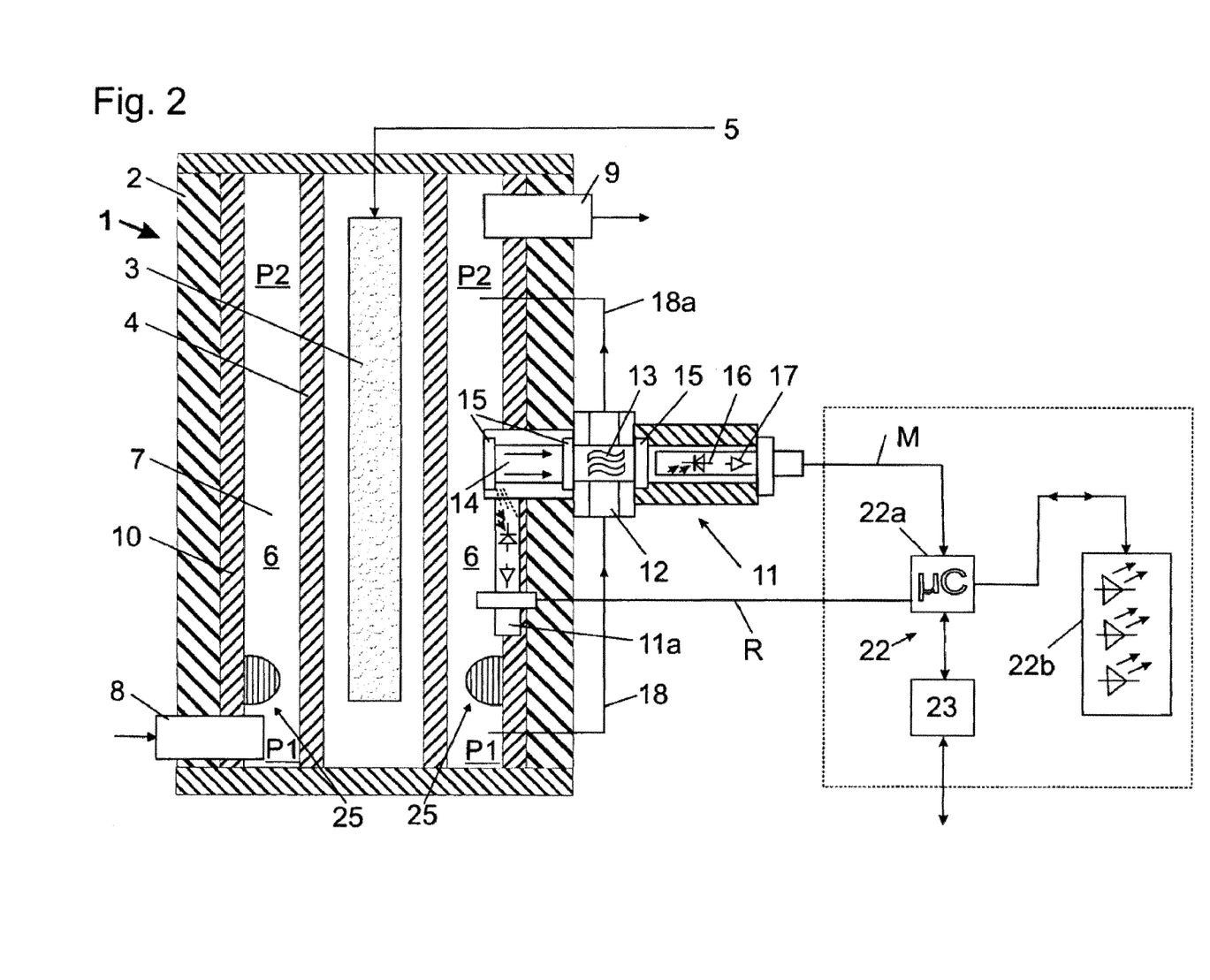
FIG. 2 shows a further embodiment of the invention with a restrictor in the chamber system.

Advantageously, provision is made for the control medium, which is acted on by the conveyor device 19 (pump 19a), to be able to be introduced in a third mode of operation into the container 2 which is provided for receiving the fluid 7, thus allowing the fluid 7 located in the container 2 or in the chamber system 6 to be transported substantially completely out of the container 2 via the outlet 9. In other words, the compressed air generated by the pump 19a can cleanse both the measuring chamber 12 and the chamber system 6 in the container 2 of dirt formed during operation. Thus, soiling of the measuring windows 15 is also substantially prevented. Provided that the fluid 7 is not excessively contaminated, the measuring device 11 or the UV probe is thus maintenance-free. As a stand-alone apparatus, the probe does not have to be operated. The quality of the fluid 7 is ascertained via the display device 22b, i.e. via an LED status display, which displays four ranges based on a traffic light system:

green: fluid 7 is in a tolerable range
green/amber: fluid 7 is at the transition from the tolerable to the non-tolerable range
red/amber: fluid 7 is at the transition from the non-tolerable to the tolerable range
red: fluid 7 is in a non-tolerable range FIG. 2 shows an alternative embodiment according to the invention. In the chamber system 6 provided for the treatment of the fluid 7, in contrast to the configuration according to FIG. 1, a device is provided for generating at least two regions having different pressure ratios P1, P2; this is made possible by the schematically illustrated restrictor 25. The restrictor 25 in the bottom region of the container 2 causes a reduction of the flow cross section for the fluid 7 which enters the chamber system 6 through the inlet 8 and leaves the chamber system 6 through the outlet 9 as a substantially sterilized fluid 7. A dynamic pressure is thus formed in the region of the container 2 that is close to the bottom, the flow cross section being narrowed in the region of the restrictor 25 and causing downstream a drop in pressure of the fluid 7, so that P1 is greater than P2. This increased pressure P1 is now utilized to continuously supply fluid 7 to the measuring chamber 12 via a line 18, wherein in the course of this process the measuring device 11 can be used to determine—preferably continuously—the corresponding measured value for the intensity and if appropriate for the spectral distribution of the light passing through the measuring windows 15 and through the partial section 13. The fluid 7 subsequently returns to the chamber system 6, into the region of the lower pressure P2, via a line 18a.

The corresponding reference value is detected in the exemplary embodiment shown by means of a separate measuring device 11a. The measuring window 15, which is adjacent to the transparent quartz glass vessel 4, is embodied as a scattering window, the photodiode of the measuring device 11a being arranged close to this window 15, so that scattered light signals (indicated by broken lines) can be detected—preferably continuously. After passing through a booster stage, the scattered light signals are supplied via a line R to the microcontroller 22a, where they are stored as a reference value. The corresponding measured values of the measuring device 11 are supplied to the microcontroller 22 via a line M, whereupon the parameters described hereinbefore can be calculated.

Figure 3:
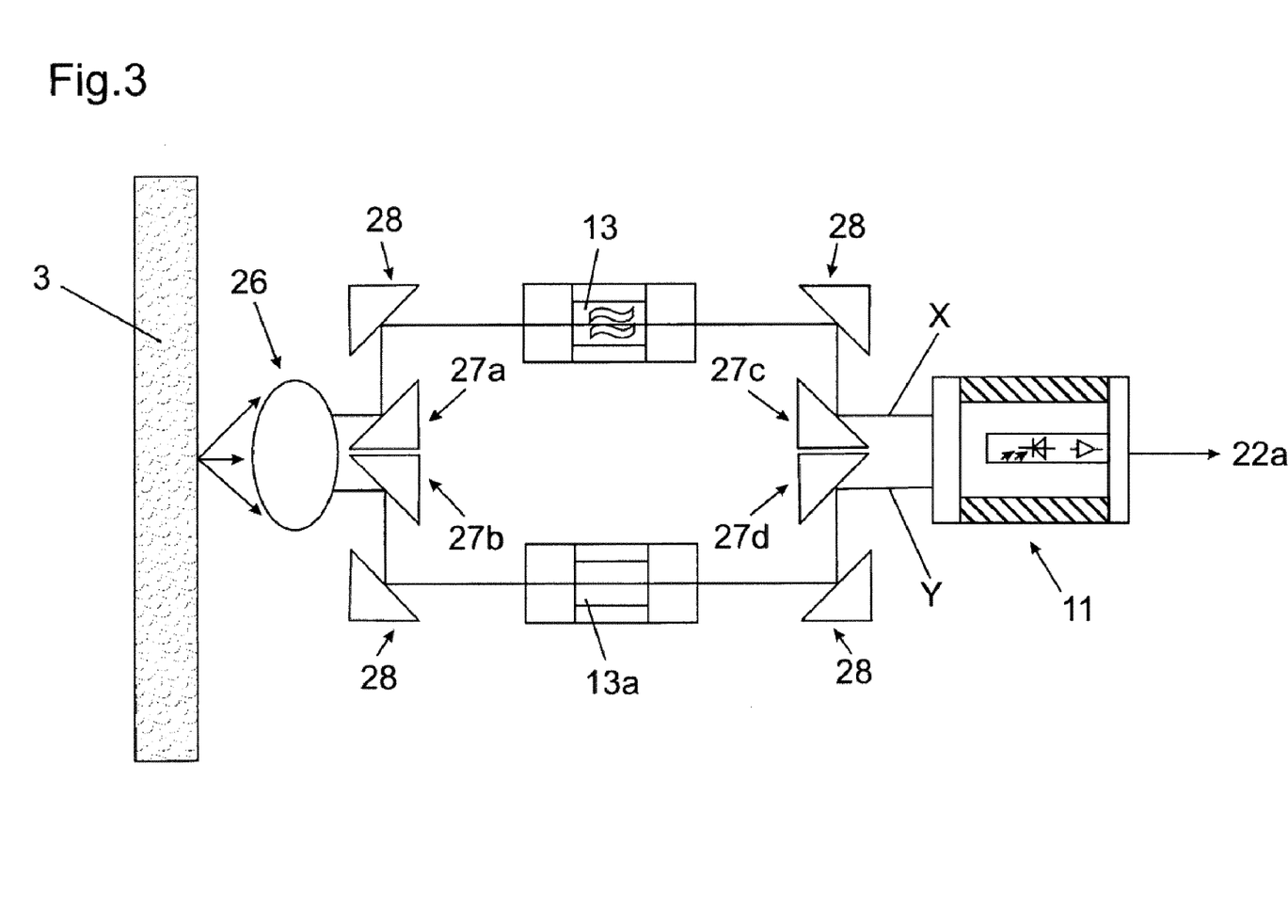
FIG. 3 shows a further embodiment of the invention with two partial sections on two separate optical paths.

FIG. 3 shows schematically a further embodiment according to the aspect of the present invention. For the sake of clarity, merely the UV light source 3 of the container 2 is shown. In this case, provision is advantageously made for a "point light" emitted by the UV light source 3 to be split into parallel light beams via a collimating lens 26. The parallel beams issuing from the collimating lens 26 are deflected onto different optical paths via a beam splitter 27a, 27b (prisms) and via deflection mirrors 28. The light is thus on the one hand guided via a partial section 13 (the fluid 7 to be sterilized flowing preferably continuously through this partial section 13) and on the other hand guided via a partial section 13a which is separate from the partial section 13 (and which the reference medium constantly fills or flows through). Subsequently, the light from the two partial sections 13, 13a is supplied to the deflection mirrors 28 which project the light onto prisms 27c and 27d. The light beam X issuing from the prism 27c is thus a measure of the quality of the fluid 7 to be sterilized, while the light beam Y is a signal which is characteristic of the reference value. The light beams X and Y can be supplied as a sum signal to the measuring device 11, the corresponding measured and reference value being detectable. These values are subsequently supplied to the microcontroller 22a. The design configuration illustrated in the figure shown has the advantage that the light from the light source 3 is irradiated from the same region of the light source 3 for detecting the measured and reference value. In this way, the same requirements or ambient conditions prevail for the detection of these values, as a result of which a direct comparison thereof is possible in a precise manner.

Figure 4A:
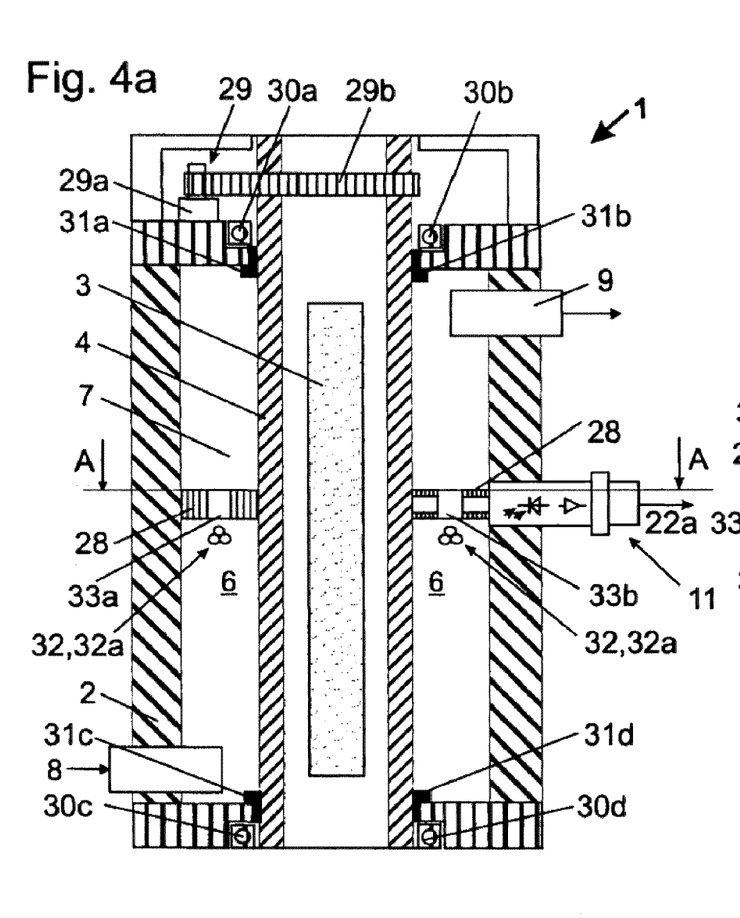
FIG. 4a, 4b are various sectional views of an alternative embodiment of the invention.
Figure 4B:
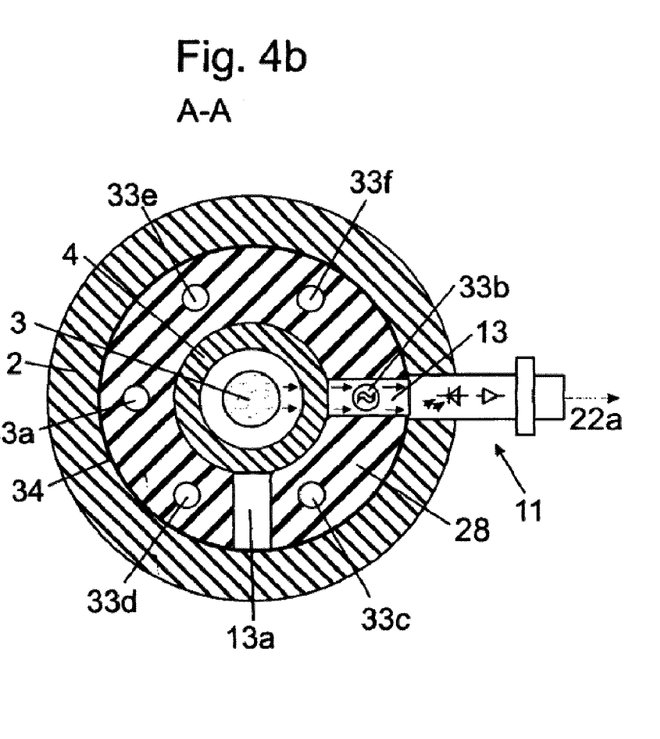

FIG. 4a and FIG. 4b show a further alternative variant of the invention. FIG. 4a is a schematic vertical section through the construction of the device 1, a longitudinally stretched UV light source 3 being surrounded by a transparent quartz glass vessel 4. In contrast to the configurations described hereinbefore, the transparent quartz glass vessel 4 is arranged so as to be able to move relative to the UV light source 3, preferably so as to be able to rotate about the UV light source 3. A disk-shaped rotor 28 is rotationally engaged with the quartz glass vessel 4, so that a schematically illustrated drive device 29 with a stepper motor 29a and a toothed belt 29b can be used to rotate the transparent quartz glass vessel 4, along with the rotor 28, about the UV light source 3. The quartz glass vessel 4 is arranged so as to be rotatable by means of bearing devices 30a-30d (for example ball bearings). Reference numerals 31a-31d denote seals, so that apart from the inlet 8 and the outlet 9, the container 2 is embodied in a fluid-tight manner. Alternatively or additionally to the drive device 29 shown for moving the quartz glass vessel 4 or the rotor 28, a device 32 can also be provided for utilizing the flow energy of the fluid 7 transported through the chamber system 6. In the exemplary embodiment shown, this device 32 comprises two impellers 32a which convert the flow energy of the fluid 7 into a rotary movement of the rotor 28. The rotor 28, which can rotate about the UV light source 3, comprises a plurality of flow channels 33a, 33b for the fluid 7, which flow channels are embodied as through-holes through the disk-shaped rotor 28. These axially extending flow channels 33a, 33b allow the fluid 7 to flow through the rotor 28 and not just through the narrow annular gap between the circumferential surface of the rotor 28 and the inner side of the container 2. A measuring device 11 (with a photodiode and a booster stage) is inserted into the container wall from the outer side of the container 2 and serves, depending on the rotary position of the rotor 28, to detect the measured value and the reference value, respectively.

FIG. 4b is a sectional view along the axis A-A according to FIG. 4a, i.e. substantially a top plan view onto the rotor 28 arranged in the container 2. Shown at the center is the UV light source 3 which is surrounded by the transparent quartz glass vessel 4 which can rotate relative to the UV light source 3. The disk-shaped rotor 28 is rotationally engaged with the quartz glass vessel 4. The rotor 28 extends, apart from the annular gap 34, substantially from the quartz glass vessel 4 up to the inner side of the container 2. Shown are the flow channels 33a-33f which penetrate the rotor 28 and generate the turbulences of the fluid 7 passing through these flow channels 33a-33f, thereby reducing the "shadow effect" and increasing the sterilization performance. The rotor 28 also has two radial holes which are offset through 90° and are denoted as partial sections 13 and 13a. The light given off by the UV light source 3 permeates on the one hand the quartz glass vessel 4 and on the other hand the partial section 13, which is filled with the fluid 7 to be sterilized, the light intensity detected by the measuring device 11 corresponding to the quality of the fluid 7 to be sterilized. In the figure shown, the rotor 28 assumes a rotary position provided for detecting the measured value. For detecting the reference value, the rotor 28 is now rotated, starting from the position shown in FIG. 4b, through 90° in the anticlockwise direction, so that the partial section 13a now opposes the measuring device 11. This partial section 13a is, in contrast to the partial section 13, sealed and filled with a reference medium, preferably air. The light from the UV light source 3, which light is given off from the same point as previously during the detection of the measured value, now strikes, after passing through the transparent quartz glass vessel 4 and through the partial section 13a, which is filled with the reference medium, the measuring device 11, the corresponding reference value being determined. As a result of a continuous rotary movement of the rotor 28—initiated by the drive device 29 and/or the device 32 for utilizing the flow energy of the fluid 7—an alternating, continuous determining of the measured value and the reference value can be provided, which, even in the case of short time lags, can be supplied without difficulty to a microcontroller 22a and be detected thereby.

Figure 5A:
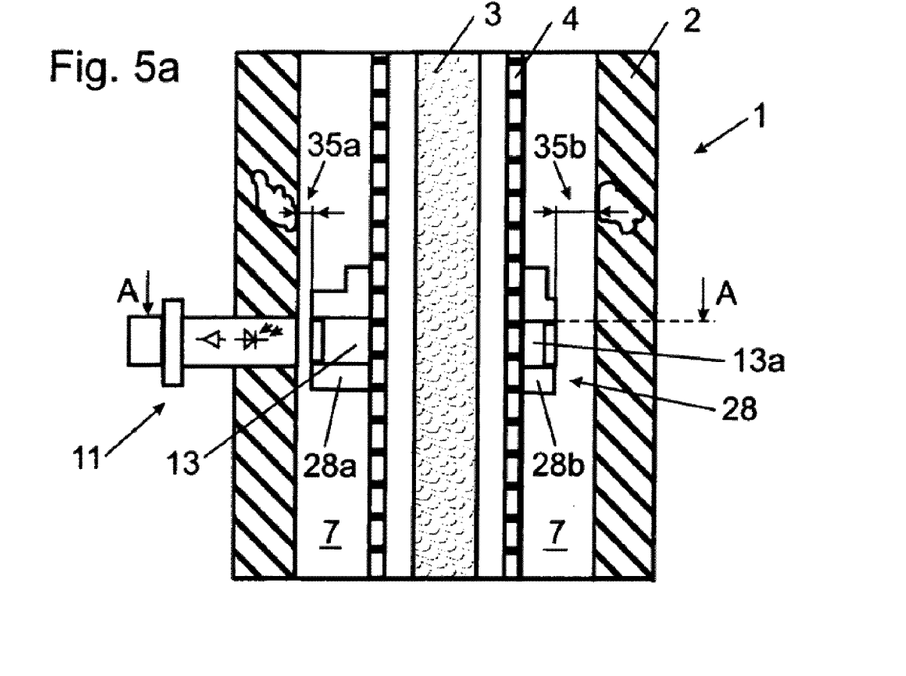
FIG. 5a, 5b show a further embodiment of the invention, wherein a rotor with rotor vanes and also additional partial sections of different length are provided.
Figure 5B:
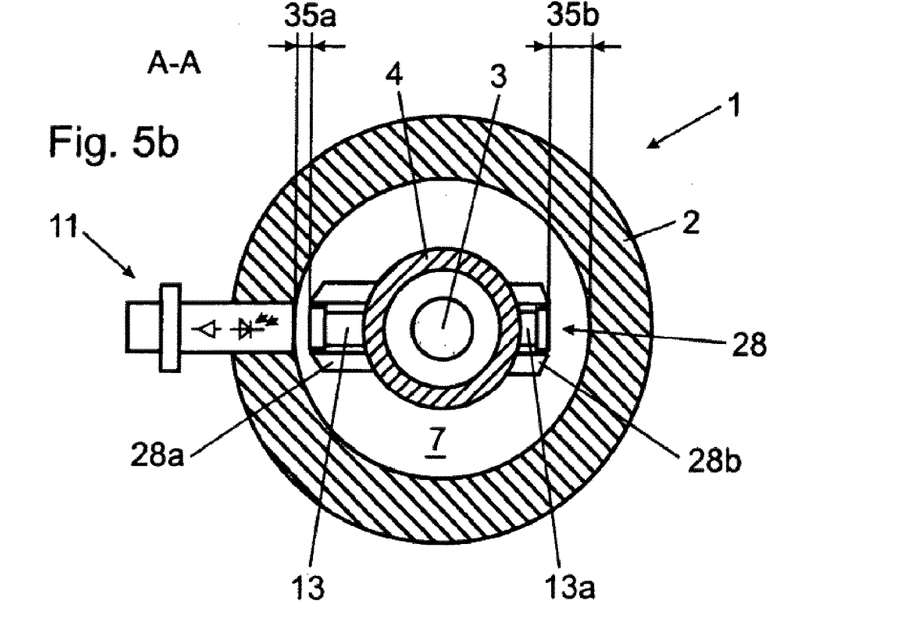

FIG. 5a and FIG. 5b are a highly schematic horizontal and vertical section through a further exemplary embodiment of the device 1. Shown is at least one UV light source 3 which is provided for the irradiation of the fluid 7 and surrounded by a quartz glass vessel 4 transmitting the UV light. The preferably cylindrical quartz glass vessel 4 is mounted so as to be able to rotate about the UV light source 3. The means for relative rotatability of the quartz glass vessel 4 may be embodied as in FIG. 4a, 4b. A rotor 28, which in the exemplary embodiment shown comprises two rotor vanes 28a, 28b of different length, is, again, fastened to the quartz glass vessel 4. The rotation of the two rotor vanes 28a, 28b brings about a turbulent flow in the sterilization zone, so that the particles of the fluid 7 are irradiated, as a result of the swirling which is brought about, by UV light from various sides, thus allowing the sterilization performance to be optimized. Partial sections 13, 13a of different length, which are each filled with a reference medium (for example air), are arranged or embodied on the two rotor vanes 28a, 28b. Between the inner side of the container 2 and the distal ends of the two rotor vanes 28a, 28b remain edge gaps which are additional partial sections 35a, 35b of different length, via which the UV light can be guided toward the measuring device 11. The position of the rotor vane 28a according to FIG. 5a and the corresponding horizontal section according to FIG. 5b (sectional plane A-A) corresponds to the operating position of the rotor 28 for determining the reference value. The UV light issuing from the UV light source 3 is transmitted by the quartz glass vessel 4 and also by the movable partial section 13, which is filled with the reference medium, and by the additional partial section 35a, allowing a corresponding reference value to be detected by the measuring device 11. If the rotor 28 is rotated, starting from the position shown in FIG. 5b, through 180°, then the shorter rotor vane 28a, having the short-term movable partial section 13a and the longer additional partial section 35b, directly opposes the measuring device 11, whereupon a corresponding measured value can be detected by the measuring device 11. Thus, as a result of the rotation of the rotor 28, both a reference value (shorter additional partial section 35a through the fluid) and a measured value (longer additional partial section 35b through the fluid) can be determined. The absorption and all the measured variables related thereto (SEC, SAC, transmission, TOC, etc.) can be computed from the reference value and the measured value.

A further advantage of the proposed device 1 consists in the fact that the surface of the rotatably mounted quartz glass vessel 4 can be continuously scanned by UV light. That is to say, the disinfecting effect of the UV light source 3 can dwindle if the outer surface of the quartz glass vessel 4 is occupied by ingredients of the fluid 7 or if the surface of the quartz glass vessel 4 is scratched. In the case of such impairment, it may occur that sufficient UV light no longer passes through the quartz glass vessel 4 into the liquid to be sterilized. The UV light from the UV light source 3 passes through the wall of the quartz glass vessel 4 and strikes the at least one measuring device 11. Any deposits and scratches at the surface of the quartz glass vessel 4 manifest themselves in a distortion of the shape of the signal received by the measuring device 11. These signal deviations are statistically evaluable, wherein a warning signal can be generated if a predefined or predefinable threshold value is exceeded.

It should be noted that the device 1 shown in the figures represents merely a possible example for carrying out the invention. The evaluation device 22 having the microcontroller 22a expediently comprises a regulator for controlling the exchange of data (programmable input/output, or PIO for short) and also a bus system, for example a serial peripheral interface (SPI). According to a further exemplary embodiment, the measuring windows 15 can also have optical fiber rods. The device 1 according to the invention is particularly suitable for the precise detection of the described parameters over relatively long periods of time, without thereby necessitating recalibration.

The invention claimed is:

1. A device for sterilizing a fluid, said device comprising:
a container for receiving the fluid;
a UV light source for the sterilization of the fluid; and
a measuring device for determining absorption properties and/or cloudiness of the fluid, the measuring device comprising a measuring chamber for receiving the fluid and/or a reference medium;
wherein a light source is associated with the measuring device such that the light from the light source leads to the measuring device in a first mode of operation at least on a partial section through the fluid, and leads to the measuring device in a second mode of operation on this partial section through the reference medium having known absorption properties and/or cloudiness; and
wherein the measuring chamber is arranged in relation to the container such that light from the UV light source is supplied to the measuring chamber via one light channel.

2. The device as claimed in claim 1, wherein precisely one measuring device is provided for the first and second mode of operation.

3. The device as claimed in claim 1, wherein the measuring chamber is arranged at least in certain regions spatially outside the container for receiving the fluid.

4. The device as claimed in claim 1, wherein the partial section is arranged in the measuring chamber, the measuring chamber being fillable in the first mode of operation with the fluid and being fillable in the second mode of operation with the reference medium.

5. The device as claimed in claim 1, wherein a sample taking device for removing fluid is provided for filling the measuring chamber, the sample taking device being configured to remove fluid from the container and supply it to the measuring chamber via a line.

6. The device as claimed in claim 5, wherein the sample taking device has a conveyor device for generating a reduced or excess pressure of a control medium in the line.

7. The device as claimed in claim 6, wherein the conveyor device is operable to transport fluid out of the measuring chamber, preferably back into the container.

8. The device as claimed in claim 6, wherein the conveyor device has at least one pump.

9. The device as claimed in claim 1, wherein, in the first mode of operation, the measuring device is configured to detect the intensity and if appropriate the spectral distribution of the light passing therethrough as a characteristic measured value.

10. The device as claimed in claim 1, wherein a reference value which is characteristic of the light irradiated from the light source can be calculated from a value, measured in the second mode of operation, for the intensity and if appropriate for the spectral distribution.

11. The device as claimed in claim 1, wherein the measuring device comprises a measuring sensor for delivering a dependent measuring signal which is characteristic of the intensity and if appropriate of the spectral composition of the measured light.

12. The device as claimed in claim 11, wherein the measuring device comprises a signal amplifying device for boosting the measuring signal.

13. The device as claimed in claim 11, wherein the measuring signal is supplied to an evaluation device.

14. The device as claimed in claim 13, wherein the evaluation device has an electronic control device for storing and processing the measuring signal.

15. The device as claimed in claim 13, wherein the evaluation device has a display device for displaying the measured measuring signals.

16. The device as claimed in claim 13, wherein the evaluation device has an interface for supplying the measuring signal to an external data processing system.

17. The device as claimed in claim 1, wherein the light source associated with the measuring device is a UV light source.

18. The device as claimed in claim 17, wherein the light source associated with the measuring device is the UV light source for the sterilization of the fluid.

19. The device as claimed in claim 1, wherein the measuring device is arranged spatially outside a chamber system of the container.

20. A device for sterilizing a fluid, said device comprising:
a container for receiving the fluid;
a UV light source for the sterilization of the fluid; and
a measuring device for determining absorption properties and/or cloudiness of the fluid,
wherein a light source is associated with the measuring device such that the light from the light source leads to the measuring device in a first mode of operation at least on a partial section through the fluid, and leads to the measuring device in a second mode of operation on this partial section through a reference medium having known absorption properties and/or cloudiness;
wherein a sample taking device for removing fluid is provided for filling a measuring chamber of the measuring device, the sample taking device being configured to remove fluid from the container and supply it to the measuring chamber via a line;
wherein the sample taking device has a conveyor device for generating a reduced or excess pressure of a control medium in the line; and
wherein the sample taking device and the container are configured such that, in a third mode of operation, the control medium acted on by the conveyor device can be introduced into the container for receiving the fluid, so that the fluid located in the container can be transported substantially completely out of the container via an outlet.

21. A device for sterilizing a fluid, said device comprising:
a container for receiving the fluid;
a UV light source for the sterilization of the fluid; and
a measuring device for determining absorption properties and/or cloudiness of the fluid,
wherein a light source is associated with the measuring device such that the light from the light source leads to the measuring device in a first mode of operation at least on a partial section through the fluid, and leads to the measuring device in a second mode of operation on this partial section through a reference medium having known absorption properties and/or cloudiness;
wherein a sample taking device for removing fluid is provided for filling a measuring chamber of the measuring device, the sample taking device being configured to remove fluid from the container and supply it to the measuring chamber via a line;
wherein the sample taking device has a conveyor device for generating a reduced or excess pressure of a control medium in the line; and
wherein the sample taking device has a fluid detector device for detecting the level of the fluid in a measuring chamber of the measuring device, wherein the conveyor device can be switched off if a predetermined level of the fluid in the measuring chamber is reached or exceeded.

22. The device as claimed in claim 21, wherein the fluid detector device has at least one sensor for detecting the level of the fluid in the measuring chamber.

23. A device for sterilizing a fluid, said device comprising:
a container for receiving the fluid;
a UV light source for the sterilization of the fluid; and
a measuring device for determining absorption properties and/or cloudiness of the fluid,
wherein a light source is associated with the measuring device such that the light from the light source leads to the measuring device in a first mode of operation at least on a partial section through the fluid, and leads to the measuring device in a second mode of operation on this partial section through a reference medium having known absorption properties and/or cloudiness, and
wherein the measuring device is configured to detect the scattered light of the light given off by the UV light source and directed toward a measuring chamber for receiving the fluid and/or reference medium, the measuring device being arranged between the UV light source and the measuring chamber for the fluid.

24. A device for sterilizing a fluid, said device comprising:
a container for receiving the fluid;
a UV light source for the sterilization of the fluid; and
a measuring device for determining absorption properties and/or cloudiness of the fluid,
wherein a light source is associated with the measuring device such that the light from the light source leads to the measuring device at least on a first partial section through the fluid, and leads to the measuring device on the first partial section or a separate second partial section through a reference medium having known absorption properties and/or cloudiness, and wherein the light from the light source can be irradiated for the first partial section and the second partial section from the same region of the light source.

25. The device as claimed in claim 24, wherein the light from the light source is guided via a beam splitter over the first partial section having a measuring chamber filled at least partly with fluid, and over the second partial section having a measuring chamber filled at least partly with the reference medium and is subsequently supplied to the measuring device via optics.

26. A device for sterilizing a fluid, said device comprising:
a chamber system for treating the fluid;
a UV light source for the sterilization of the fluid; and
a measuring device for determining absorption properties and/or cloudiness of the fluid,
wherein a light source is associated with the measuring device such that the light from the light source leads to the measuring device through the fluid or a reference medium having known absorption properties and/or cloudiness; and
wherein a restrictor for generating at least two regions having different pressure ratios is arranged in the chamber system, wherein fluid from the region of the higher pressure ratio of the fluid is supplied to the measuring device and is subsequently supplied to the region of the lower pressure ratio of the fluid.

27. A device for sterilizing a fluid, said device comprising:
a chamber system for treating the fluid;
a UV light source for the sterilization of the fluid;
a measuring device for determining absorption properties and/or cloudiness of the fluid; and
at least one partial section movable relative to the UV light source, is provided in the chamber system;
wherein a light source is associated with the measuring device such that the light from the light source leads to the measuring device through the fluid or a reference medium having known absorption properties and/or cloudiness; and
wherein, in a first operating position of the at least one partial section, the light from the UV light source is supplied to the measuring device over the at least one partial section filled with the fluid to be sterilized and wherein, in a second operating position of the at least one partial section, the light from the UV light source can be supplied to the measuring device over the at least one partial section filled with a reference medium.

28. The device as claimed in claim 27, wherein the at least one movable partial section is arranged or embodied in or on a rotor which can rotate about the UV light source.

29. The device as claimed in claim 28, wherein the rotor is arranged on a quartz glass vessel surrounding the UV light source at least in certain regions, the quartz glass vessel being arranged so as to be able to move relative to the UV light source so as to be able to rotate about the UV light source.

30. The device as claimed in claim 29, wherein, in a rotary position of the rotor, the light emitted by the UV light source is supplied to the measuring device through a wall of the quartz vessel surrounding the UV light source at least in certain regions.

31. The device as claimed in claim 28, wherein the rotor comprises at least two rotor vanes of different length, the at least one movable partial section being arranged or embodied on or in a rotor vane.

32. The device as claimed in claim 28, wherein the rotor is movable via an electric motor.

33. The device as claimed in claim 32, wherein the drive device has at least one impeller for utilizing the flow energy of the fluid, the rotor being movable via the at least one impeller.

34. A device for sterilizing a fluid, said device comprising:
a chamber system for treating the fluid;
a UV light source for the sterilization of the fluid;
a measuring device for determining absorption properties and/or cloudiness of the fluid; and
at least one movable partial section,
wherein a light source is associated with the measuring device such that the light from the light source leads to the measuring device through the fluid or a reference medium having known absorption properties and/or cloudiness,
wherein, in a first operating position of the at least one movable partial section, the light emitting from the UV light source can be supplied to the measuring device over a first additional partial section filled with the fluid to be sterilized, and
wherein, in a second operating position of the at least one movable partial section, the light emitting from the UV light source can be supplied to the measuring device over a second additional partial section filled with the fluid to be sterilized, the first additional partial section and the second additional partial section having different lengths.

* * * * *